US011788999B2

(12) United States Patent
Wei et al.

(10) Patent No.: US 11,788,999 B2
(45) Date of Patent: Oct. 17, 2023

(54) SENSOR DEVICE AND GAS MONITORING SYSTEM

(71) Applicant: Panasonic Intellectual Property Management Co., Ltd., Osaka (JP)

(72) Inventors: Zhiqiang Wei, Osaka (JP); Shinichi Yoneda, Kyoto (JP); Ryoichi Suzuki, Osaka (JP); Shunsaku Muraoka, Osaka (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 660 days.

(21) Appl. No.: 16/712,540

(22) Filed: Dec. 12, 2019

(65) Prior Publication Data

US 2020/0116685 A1 Apr. 16, 2020

Related U.S. Application Data

(63) Continuation of application No. PCT/JP2018/032841, filed on Sep. 5, 2018.

(30) Foreign Application Priority Data

Oct. 2, 2017 (JP) ................................ 2017-192650

(51) Int. Cl.
*G01M 3/28* (2006.01)
*G01N 33/00* (2006.01)
(Continued)

(52) U.S. Cl.
CPC ........ *G01N 33/005* (2013.01); *G01M 3/2892* (2013.01); *H04L 67/12* (2013.01); *H04W 84/18* (2013.01)

(58) Field of Classification Search
CPC ........ G01M 3/04; G01M 3/26; G01M 3/2853; G01M 3/20; G01M 3/183; G01M 3/182
(Continued)

(56) References Cited

U.S. PATENT DOCUMENTS 2,658,434 A * 11/1953 Miller ....................... F17D 5/02
73/40.5 R
2,951,764 A * 9/1960 Chase .................. G01N 31/222
426/88
(Continued)

FOREIGN PATENT DOCUMENTS

CN 202903160 U 4/2013
CN 203849605 U 9/2014
(Continued)

OTHER PUBLICATIONS

ESPACENET Machine Translation of JP 2002116268 A1 Which Originally Published On Apr. 19, 2002. (Year: 2002).*
(Continued)

*Primary Examiner* — David A. Rogers
(74) *Attorney, Agent, or Firm* — McDermott Will & Emery LLP

(57) ABSTRACT

A gas monitoring system includes at least one sensor device that detects gas and outputs a detection result; and a gateway that receives the detection result. The at least one sensor device includes a sensor module having a gas sensor that detects gas; an analog-to-digital (A/D) converter that processes the detection result outputted from the gas sensor; a communication module that communicates with the sensor module and transmits information processed by the A/D converter exteriorly of the at least one sensor device; a power source that is an electric power source of the sensor module; and a power source that is an electric power source of the communication module.

41 Claims, 10 Drawing Sheets

(51) Int. Cl.
    *H04L 67/12*     (2022.01)
    *H04W 84/18*     (2009.01)

(58) Field of Classification Search
    USPC .................................................. 73/40–49.8
    See application file for complete search history.

(56) References Cited

U.S. PATENT DOCUMENTS

| | | | |
|---|---|---|---|
| 3,220,259 A * | 11/1965 | Beyer | G01N 33/02 374/E3.004 |
| 3,531,264 A * | 9/1970 | Greipel | G01M 3/02 137/551 |
| 3,597,973 A * | 8/1971 | Ryder | G01N 9/18 73/447 |
| 3,695,903 A * | 10/1972 | Telkes et al. | G01K 3/04 374/162 |
| 3,754,275 A * | 8/1973 | Carter | G01N 29/30 324/67 |
| 4,020,697 A * | 5/1977 | Jander | G01N 1/2294 73/40.7 |
| 4,083,229 A * | 4/1978 | Anway | G01M 3/243 73/592 |
| 4,305,068 A * | 12/1981 | Klein | G01M 3/045 73/40 |
| 4,452,091 A * | 6/1984 | Richers | G01V 9/007 73/864.74 |
| 4,455,863 A * | 6/1984 | Huebler | G01M 3/243 73/579 |
| 4,644,354 A * | 2/1987 | Kidd | B67D 7/04 340/870.27 |
| 4,709,577 A * | 12/1987 | Thompson | G01M 3/226 73/40.7 |
| 4,725,551 A * | 2/1988 | Thompson | G01M 3/20 73/40.7 |
| 4,728,941 A * | 3/1988 | Andrejasich | G01N 27/06 73/40 |
| 4,754,136 A * | 6/1988 | Blakely | G01M 3/20 250/390.05 |
| 4,770,028 A * | 9/1988 | Flippo, Jr. | G01M 3/20 73/40.7 |
| 5,003,813 A * | 4/1991 | Hayes | G01M 3/02 340/605 |
| 5,301,632 A * | 4/1994 | Cayol | G01K 11/06 374/E11.006 |
| 5,744,700 A * | 4/1998 | Carme | G01M 3/243 73/40.5 A |
| 5,889,217 A * | 3/1999 | Rossabi | E02D 1/025 73/864.74 |
| 5,922,943 A * | 7/1999 | Chapman, IV | G01M 3/226 73/40.7 |
| 5,922,974 A * | 7/1999 | Davison | G01N 1/405 73/864.74 |
| 5,974,862 A * | 11/1999 | Lander | G01M 3/243 73/592 |
| 6,236,941 B1 * | 5/2001 | Kram | G01N 33/24 73/84 |
| 6,262,659 B1 | 7/2001 | Korkosz et al. | |
| 6,679,070 B1 * | 1/2004 | Liberman | A23L 3/36 374/E11.006 |
| 6,695,959 B2 * | 2/2004 | Kiesele | G01N 27/4045 204/415 |
| 6,719,068 B2 * | 4/2004 | Jonsson | E21B 47/13 73/866.5 |
| 6,724,481 B2 * | 4/2004 | Makino | G01N 21/3504 356/437 |
| 6,725,705 B1 * | 4/2004 | Huebler | G01M 3/243 73/592 |
| 6,891,838 B1 * | 5/2005 | Petite | H04L 12/2836 340/870.02 |
| 6,895,069 B2 * | 5/2005 | Kim | G01D 5/28 377/16 |
| 6,898,962 B2 * | 5/2005 | Jax | G01M 3/22 73/40 |
| 6,914,533 B2 * | 7/2005 | Petite | G01V 1/37 340/630 |
| 6,920,778 B2 * | 7/2005 | Koike | G01M 3/3254 73/49.2 |
| 6,975,236 B2 * | 12/2005 | Staples | G08B 21/20 73/1.73 |
| 6,978,688 B2 * | 12/2005 | Engebretson | E21B 49/084 73/863.23 |
| 6,978,794 B2 * | 12/2005 | Dukes | A01G 25/167 239/69 |
| 7,110,779 B2 * | 9/2006 | Billhartz | H04W 64/00 455/456.2 |
| 7,187,299 B2 * | 3/2007 | Kunerth | G01M 11/30 340/539.22 |
| 7,347,643 B2 * | 3/2008 | Jeong | E01F 9/559 340/928 |
| 7,520,186 B2 * | 4/2009 | Risk | G01N 33/24 73/864.74 |
| 7,788,970 B2 * | 9/2010 | Hitt | A01G 25/167 73/73 |
| 8,707,762 B2 * | 4/2014 | Pfanstiehl | G01M 3/047 73/29.04 |
| 8,712,692 B2 * | 4/2014 | Risk | G01N 1/2294 73/23.32 |
| 9,279,732 B2 * | 3/2016 | Parker | G01K 11/06 |
| 10,060,578 B2 * | 8/2018 | Battaglini | H04L 67/12 |
| 10,085,393 B2 * | 10/2018 | Hill | H04Q 9/00 |
| 10,280,747 B2 * | 5/2019 | AbuAli | E21B 47/10 |
| 10,337,948 B2 * | 7/2019 | Heimer | G01M 3/3272 |
| 10,732,065 B2 * | 8/2020 | Inkpen | G01M 3/18 |
| 10,754,360 B2 * | 8/2020 | Zokaei | G05D 7/0635 |
| 11,048,279 B2 * | 6/2021 | Samburg | G05D 9/12 |
| 11,561,137 B1 * | 1/2023 | Al Ahbabi | G01K 11/06 |
| 2001/0002970 A1 * | 6/2001 | Pizzorni | G01M 3/226 405/128.3 |
| 2004/0004554 A1 | 1/2004 | Srinivasan et al. | |
| 2005/0021724 A1 | 1/2005 | Kung et al. | |
| 2007/0132601 A1 | 6/2007 | Al-Wehebi | |
| 2008/0079565 A1 | 4/2008 | Koyama | |
| 2008/0174282 A1 | 7/2008 | Kano et al. | |
| 2013/0269440 A1 * | 10/2013 | Maruta | G01M 3/183 73/592 |
| 2014/0232555 A1 | 8/2014 | Aakvaag et al. | |
| 2017/0131227 A1 * | 5/2017 | Homma | H01M 8/0444 |
| 2017/0268954 A1 * | 9/2017 | Ocalan | H04W 84/18 |
| 2017/0269043 A1 * | 9/2017 | Homma | G01N 33/005 |

FOREIGN PATENT DOCUMENTS

| | | |
|---|---|---|
| EP | 2752525 A1 | 7/2014 |
| JP | S61-60199 A | 3/1986 |
| JP | S62115352 A | 5/1987 |
| JP | H09-89705 A | 4/1997 |
| JP | H10-283586 A | 10/1998 |
| JP | H11-101705 A | 4/1999 |
| JP | H11-201858 A | 7/1999 |
| JP | 2002-056487 A | 2/2002 |
| JP | 2002-116268 A | 4/2002 |
| JP | 2002-157666 A | 5/2002 |
| JP | 2004-515757 A | 5/2004 |
| JP | 2005-020929 A | 1/2005 |
| JP | 2005-045784 A | 2/2005 |
| JP | 2006-349629 A | 12/2006 |
| JP | 2008-099470 A | 4/2008 |
| JP | 2008-102811 A | 5/2008 |
| JP | 2008-109847 A | 5/2008 |
| JP | 2008-141234 A | 6/2008 |
| JP | 2009-520263 A | 5/2009 |
| JP | 2009-174895 A | 8/2009 |
| JP | 2015-084147 A | 4/2015 |
| JP | 5953371 B2 | 7/2016 |
| WO | 02/46701 A2 | 6/2002 |
| WO | 2007/070149 A1 | 6/2007 |

(56) References Cited

FOREIGN PATENT DOCUMENTS

WO    2012/175933 A1    12/2012
WO    2013/002211 A1    1/2013

OTHER PUBLICATIONS

Chinese Office Action issued in corresponding Chinese Patent Application No. 201880038600.3, dated Sep. 24, 2020, with English Search report.
International Search Report issued in corresponding International Patent Application No. PCT/JP2018/032841, dated Dec. 11, 2018, with English translation.

* cited by examiner

SENSOR DEVICE AND GAS MONITORING SYSTEM

CROSS REFERENCE TO RELATED APPLICATIONS

This application is a U.S. continuation application of PCT International Patent Application Number PCT/JP2018/032841 filed on Sep. 5, 2018, claiming the benefit of priority of Japanese Patent Application Number 2017-192650 filed on Oct. 2, 2017, the entire contents of which are hereby incorporated by reference.

BACKGROUND

1. Technical Field

The present disclosure relates to a sensor device and gas monitoring system that detect leaked gas underground.

2. Description of the Related Art

In recent years, strenuous efforts aimed at the realization of a hydrogen energy-based society have been made. In particular, fuel-cell vehicles fueled with hydrogen, hydrogen stations, etc. are being introduced to the market, and subsequently infrastructure for supplying hydrogen, e.g. pipelines, are being installed. Under these circumstances is the importance for sensors that detects hydrogen leaks on the rise in order to guarantee the safety and security of the hydrogen energy-based society.

In the sensor system recited in Japanese Unexamined Patent Application Publication (Translation of PCT Application) No. 2004-515757, for example, multiple sensors are disposed underground (in concrete) in advance. The multiple sensors monitor for multiple parameters relating to gas and environment unrelated to gas, and wirelessly output the monitored parameters exteriorly of the multiple sensors after having been processed.

It is not possible to replace or inspect conventional gas detection systems since their sensors are disposed in concrete in advance. They therefore face the issue that it is not possible to apply convention gas detection systems to gas monitoring that monitor for gas leaks at all times.

The present disclosure provides a sensor device and a gas monitoring system that are capable of monitoring for gas leaks at all times.

SUMMARY

In order to solve the above problem, a sensor device according to an aspect of the present disclosure detects a gas leak underground and includes a sensor module including a first sensor that detects gas; a processing circuit that processes a detection result outputted from the first sensor; a communication module that communicates with the sensor module and transmits information processed by the processing circuit exteriorly of the sensor device; a first power source that is an electric power source of the sensor module; and a second power source that is an electric power source of the communication module.

A gas monitoring system according to an aspect of the present disclosure detects a gas leak underground and includes at least one sensor device that detects gas and outputs a detection result; and a gateway that receives the detection result. The at least one sensor device includes a sensor module having a first sensor that detects gas; a processing circuit that processes the detection result outputted from the first sensor; a communication module that communicates with the sensor module and transmits information processed by the processing circuit exteriorly of the at least one sensor device; a first power source that is an electric power source of the sensor module; and a second power source that is an electric power source of the communication module.

The present disclosure makes it possible to provide a sensor device and a gas monitoring system that are capable of monitoring for gas leaks at all times.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENTS

Figure 1:
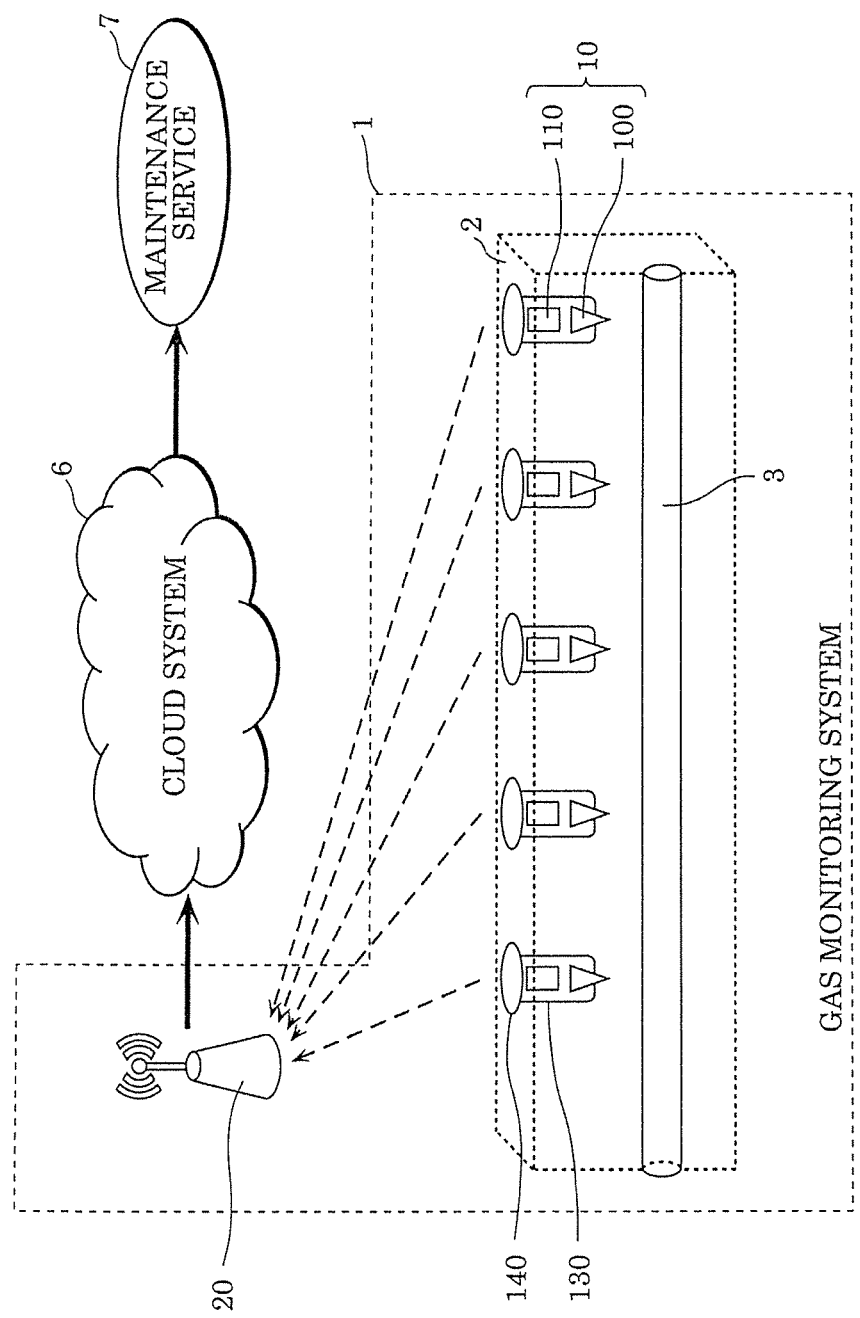
FIG. 1 is an overall diagram of a gas monitoring system according to Embodiment 1.

Hereinafter, embodiments in the present disclosure will be described with reference to the drawings.

Note that in each drawing, components representing configurations, operations, and effects that are substantially the same as components described previous thereto have the same reference numerals and descriptions are omitted. Numerical values, materials, components, compositions, shapes, deposition methods, connection relationships of the components, and the like mentioned below are mere examples for concretely describing the embodiments in the present disclosure and are not intended to limit the present disclosure. Components in the following embodiments not mentioned in any of the independent claims that define the broadest concepts are described as optional elements.

Embodiment 1

1. Configuration of Gas Monitoring System

FIG. 1 is an overall diagram of gas monitoring system 1 according to Embodiment 1. Gas monitoring system 1 is a system that detects gas leaks of gas supplied by pipeline 3 buried in ground 2 at all times. Hereinafter, gas monitoring system 1 that detects hydrogen leaks will be described with the gas supplied by pipeline 3 being described as gas containing hydrogen. Gas containing hydrogen is a collective term for gas including molecules with hydrogen atoms, and can include, for example, hydrogen, methane and alcohol.

As illustrated in FIG. 1, gas monitoring system 1 includes at least one sensor device 10 buried in ground 2, and gateway 20. Sensor device 10 is disposed, for example, above pipeline 3 that is a transportation route for gas containing hydrogen. Sensor device 10 detects gas containing hydrogen leaked from pipeline 3. A configuration of sensor device 10 will be described in more detail later.

Sensor device 10 transmits and receives data to and from gateway 20. For example, information about the gas leak detected by sensor device 10 and information relating to a gas leak position is transmitted from sensor device 10 to gateway 20.

Gateway 20 is a relay device such as a base station or a router. A Global Positioning System (GPS) module is disposed in gateway 20. Gateway 20 detects the gas leak position using the GPS module.

The information about the gas leak transmitted to gateway 20 is transmitted from gateway 20 to maintenance service 7 via cloud system 6. This enables maintenance service 7 to take measures with regard to the gas leak since it is possible to know the presence of the gas leak and the gas leak position.

2. Configuration of Sensor Device

Figure 2:
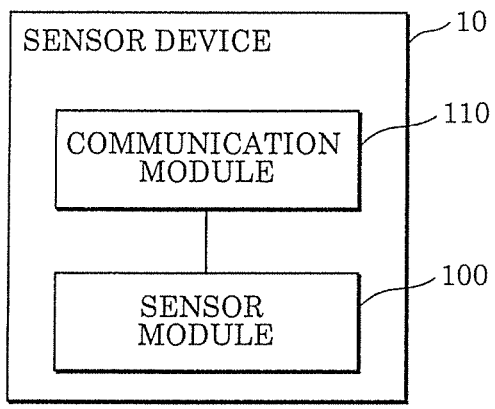
FIG. 2 is a block diagram showing a configuration of a sensor device according to Embodiment 1.

FIG. 2 is a block diagram showing a configuration of sensor device 10 according to the present embodiment. As illustrated in FIG. 1 and FIG. 2, sensor device 10 includes sensor module 100 and communication module 110. Configurations of sensor module 100 and communication module 110 will be described in more detail later.

As illustrated in FIG. 1, sensor module 100 and communication module 110 are, for example, disposed in hand hole 130 buried in ground 2. Hand hole 130 has enough space in an interior thereof making it possible to insert a hand in through an opening and operate sensor device 10. Lid 140 that covers the opening of hand hole 130 is disposed above hand hole 130. In other words, lid 140 is disposed on a surface of ground 2.

2-1. Configuration of Sensor Module

Figure 3A:
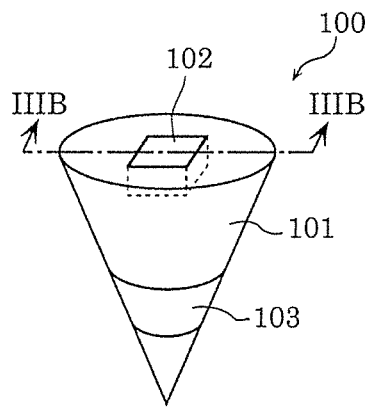
FIG. 3A is a perspective view of a configuration of the sensor device according to Embodiment 1.
Figure 3B:
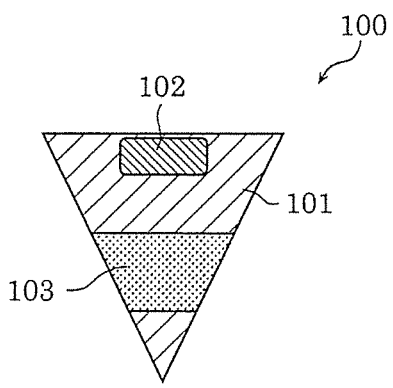
FIG. 3B is a cross-sectional view of the sensor device along line IIIB-IIIB in FIG. 3A.
Figure 4:
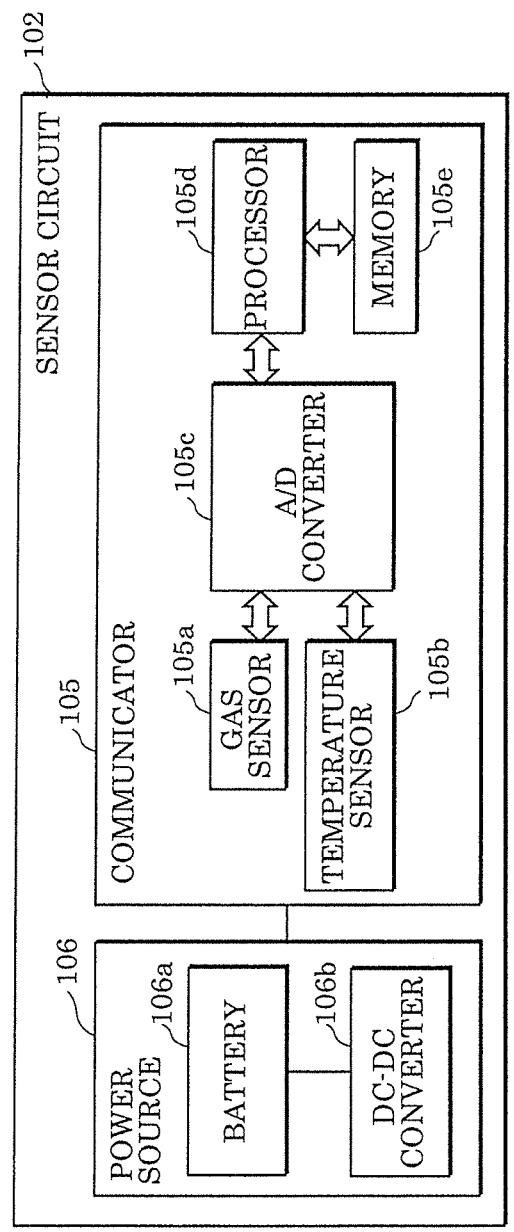
FIG. 4 is a block diagram showing a configuration of a sensor circuit according to Embodiment 1.

Hereinafter, the configuration of sensor module 100 will be described. FIG. 3A is a perspective view of the configuration of sensor device 10 according to the present embodiment. FIG. 3B is a cross-sectional view of sensor device 10 along line IIIB-IIIB in FIG. 3A. FIG. 4 is a block diagram showing a configuration of sensor circuit 102 according to the present embodiment.

As illustrated in FIG. 3A and FIG. 3B, sensor module 100 includes casing 101, sensor circuit 102, and filter 103.

Casing 101 includes, for example, an aluminum alloy, and as illustrated in FIG. 3A, is conical. Note that since sensor device 10 is disposed as a drain plug on a weep hole of hand hole 130, as will be described later, casing 101 is conical. However, casing 101 is not limited in shape and may also be pyramidal or have any other type of shape.

Sensor circuit 102 is disposed on a bottom surface of the conical casing 101. As illustrated in FIG. 4, sensor circuit 102 includes detector 105 and power source 106. Detector 105 includes gas sensor 105a, temperature sensor 105b, analog-to-digital (A/D) converter 105c, processor 105d, and memory 105e.

Gas sensor 105a is a hydrogen sensor that detects hydrogen molecules. In the present embodiment, gas sensor 105a is a first sensor. Gas sensor 105a includes two electrodes that face each other, and a metal-oxide layer disposed between the two electrodes.

One of the two electrodes includes a material having a catalytic action in which hydrogen atoms are dissociated from gas molecules with hydrogen atoms, e.g. platinum (Pt), iridium (Ir), palladium, (Pd), or an alloy including at least one of these.

The other of the two electrodes includes a material with a lower standard electrode potential than a metal including a metal oxide, e.g. tungsten (W), nickel (Ni), tantalum (Ta), titanium (Ti), aluminum (Al), tantalum nitride (TaN), or a titanium nitride (TiN). Note that standard electrode potential indicates being more difficult to oxidize with an increase in this value. The other of the two electrodes may also include a material having a catalytic action in which hydrogen atoms are dissociated from gas molecules with hydrogen atoms, e.g. platinum (Pt), iridium (Ir), palladium, (Pd), or an alloy including at least one of these.

The metal-oxide layer includes, for example, an oxide containing one metal selected from (i) metals capable of being in an oxidation state generally represented by transition metals, (ii) tin, and (iii) aluminum. The parent metal of the metal oxide may be selected from at least one of (i) a transition metal such as tantalum (Ta), hafnium (Hf), titanium (Ti), zirconium (Zr), niobium (Nb), tungsten (W), nickel (Ni), iron (Fe), chromium (Cr), cobalt (Co), manganese (Mn), vanadium (V), cerium (Ce), or copper (Cu), (ii) tin (Sri), and (iii) aluminum (Al).

Note that the metal-oxide layer may be one layer, and may also have a two-layered structure including two metal-oxide layers containing different degrees of oxygen. The metal-oxide layer may also include an oxygen-deficient metal oxide.

Temperature sensor 105b detects a temperature as at least one parameter relating a surrounding environment in which sensor device 10 is disposed. In the present embodiment, temperature sensor 105b is a second sensor. For example, a thermocouple is used for temperature sensor 105b. By disposing temperature sensor 105b, detector 105 is capable of detecting leaks of gas containing hydrogen or any other type of malfunction from a temperature change in the surrounding environment of sensor device 10.

Note that the second sensor is not limited to being a temperature sensor, and may be, for example, at least one of a temperature sensor, a humidity sensor, and a pressure sensor. The second sensor may also be a combination of the temperature sensor, humidity sensor, and pressure sensor. The second sensor may also be a water immersion sensor that detects that sensor device 10 is immersed in water, as will be described later.

Temperature sensor 105b is disposed below gas sensor 105a. This makes it possible to limit damage to gas sensor 105a due to an anomaly since it is possible to detect the anomaly from a temperature change detected by temperature sensor 105b before the anomaly is detected by gas sensor 105a. This is not limited to temperature sensor 105b, and a humidity sensor, pressure sensor, water immersion sensor, etc. may also be disposed below gas sensor 105a, similar to temperature sensor 105b. For example, when a water immersion sensor is disposed below gas sensor 105a, it is possible to prevent sensor module 100 and gas sensor 105a from malfunctioning by being immersed in water. Note that in this case, the water immersion sensor may be disposed proximate to a top of casing 101.

A/D converter 105c mutually converts an analog signal and a digital signal between gas sensor 105a, temperature sensor 105b, and the processor. In the present embodiment, A/D converter 105c is a processing circuit. A/D converter 105c converts analog data, e.g. a hydrogen amount detected by gas sensor 105a and a temperature detected by temperature sensor 105b, to digital data and supplies the digital data to processor 105d.

Processor 105d processes a detection result, e.g. a hydrogen amount detected by gas sensor 105a and a temperature detected by temperature sensor 105b, and outputs the detection result exteriorly of sensor module 100. Processor 105d encrypts the detection result of gas sensor 105a and temperature sensor 105b, and outputs the encrypted detection result exteriorly of sensor module 100. As will be described later, sensor module 100 is connected to communication module 110 by a communication wire, and processor 105d transmits the encrypted detection result to communication module 110 via the communication wire. At this point, processor 105d may transmits the detection result to communication module 110 once or multiple times.

Memory 105e is a storage that stores the detection result of gas sensor 105a and temperature sensor 105b outputted from processor 105d. In the present embodiment, memory 105e is a first memory. Memory 105e may contain the detection result of gas sensor 105a and temperature sensor 105b that is encrypted in processor 105d. The detection result stored in memory 105e is read by processor 105d, and output to communication module 110. At this point, sensor module 100 may output each instance of the detection result to communication module 110, and may also output only a portion of the detection results to communication module 110, e.g. only when gas containing hydrogen is detected.

In sensor circuit 102, power source 106 supplies electric power to detector 105. In the present embodiment, power source 106 is a first power source. Power source 106 includes battery 106a and direct current-to-direct current (DC) converter 106b.

Battery 106a supplies electric power. DC-to-DC converter 106b converts a DC voltage outputted from battery 106a to a predetermined DC voltage, and supplies the predetermined DC voltage to detector 105.

Filter 103 is a waterproof filter that prevents water from entering sensor module 100. Filter 103 includes, for example, a polytetrafluoroethylene (PTFE) porous film. Filter 103 is disposed below sensor circuit 102 in sensor module 100 and has a predetermined thickness. This makes it possible to limit water from infiltrating sensor circuit 102 from the top of the conical casing 101 contacting ground 2. As such, it is possible to limit sensor circuit 102 from malfunctioning. Note that filter 103 is not limited to being a waterproof filter and may also be a dustproof filter.

2-2. Configuration of Communication Module

Figure 5:
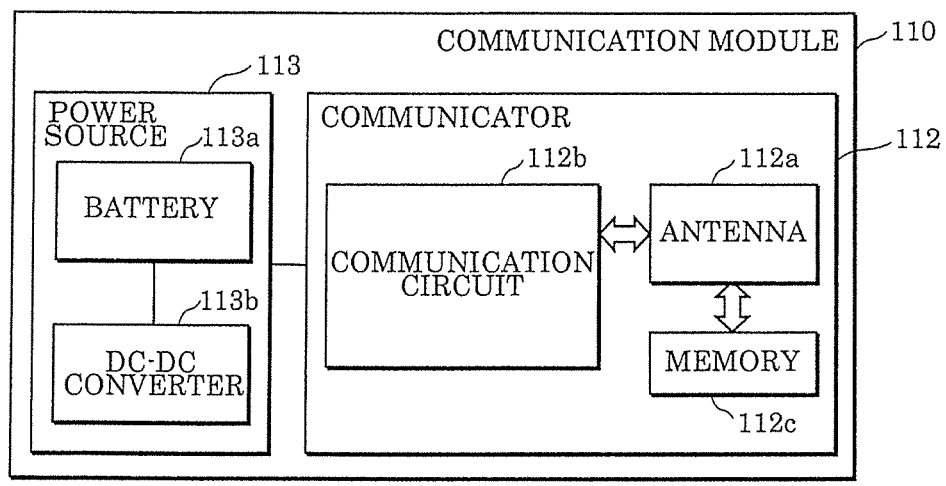
FIG. 5 is a block diagram showing a configuration of a communication module according to Embodiment 1.

The configuration of communication module 110 will be described next. FIG. 5 is a block diagram showing the configuration of communication module 110 according to the present embodiment.

Communication module 110 includes communicator 112 and power source 113.

Communicator 112 includes antenna 112a, communication circuit 112b, and memory 112c. Communication circuit 112b transmits and receives a signal to and from gateway 20 via antenna 112a. Communication circuit 112b receives, via the above-mentioned communication wire, the detection result of gas sensor 105a and temperature sensor 105b that is outputted from sensor module 100.

Memory 112c contains the detection result received from sensor module 100. In the present embodiment, memory 112c is a second memory. The detection result stored in memory 112c is read by communication circuit 112b and transmitted to gateway 20.

Power source 113 supplies electric power to communicator 112. In the present embodiment, power source 113 is a second power source. Power source 113 includes battery 113a and DC-to-DC converter 113b. A configuration of power source 113 is the same as the above-mentioned power source 106 and detailed description thereof is omitted.

2-3. Arrangement of Sensor Module and Communication Module

Figure 6:
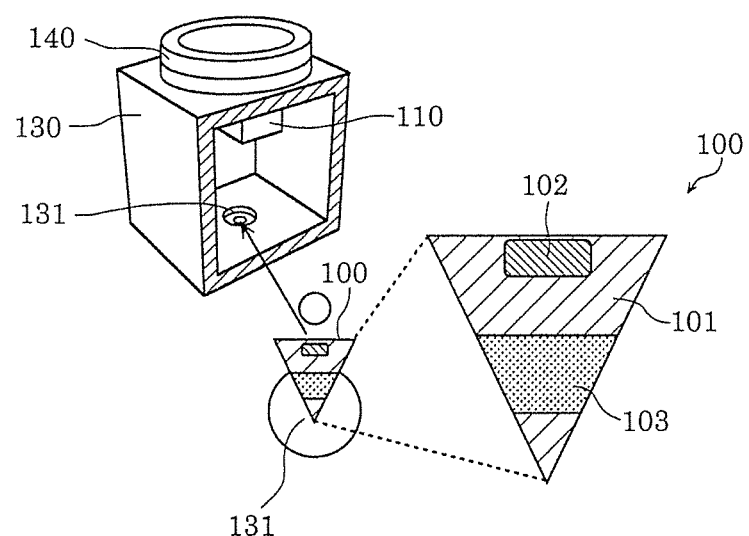
FIG. 6 is a diagram showing an arrangement of a sensor module and the communication module according to Embodiment 1.

A positional relationship between sensor module 100 and communication module 110 will be described next. FIG. 6 is a diagram showing an arrangement of sensor module 100 and communication module 110 according to the present embodiment.

As stated above, sensor module 100 and communication module 110 are disposed in hand hole 130.

As illustrated in FIG. 6, hand hole 130 has a space in the interior thereof. An opening is disposed above hand hole 130. Lid 140 covers the opening of hand hole 130. Weep hole 131 for exhausting water that has entered the interior of hand hole 130 to the outside thereof is disposed on a base of hand hole 130.

Sensor device 10 includes, in hand hole 130, one communication module 110 and one sensor module 100 corresponding to the one communication module 110. Note that sensor device 10 may include one communication module 110 and multiple sensor modules 100 corresponding to the one communication module 110.

Sensor module 100 and communication module 110 are separately disposed. By separately disposing sensor module 100 and communication module 110, it is possible to only replace the malfunctioning sensor module 100 or communication module 110 when sensor module 100 or communication module 110 is malfunctioning.

Sensor module 100 is disposed in weep hole 131 that is disposed in the base of hand hole 130. More specifically, in sensor module 100, the top of the conical casing 101 points from the interior of hand hole 130 toward an outside of weep hole 131. This enables sensor module 100 to function as the drain plug of hand hole 130.

Note that sensor module 100 may be disposed in a place other than weep hole 131. For example, the interior of hand hole 130 may have a dedicated hole to dispose sensor module 100 in, and sensor module 100 may be disposed in the hole.

Communication module 110 is disposed above sensor module 100. As illustrated in FIG. 6, for example, communication module 110 is disposed on a surface of lid 140 that faces the interior of hand hole 130. With this, communication module 110 is disposed above sensor module 100.

Therefore, sensor module 100 is disposed more proximate to pipeline 3 than communication module 110. As such, it is possible to detect gas containing hydrogen with high sensitivity and high precision.

Note that sensor module 100 and communication module 110 may be separately disposed, and may also be integrally disposed, as will be described later.

Figure 7:
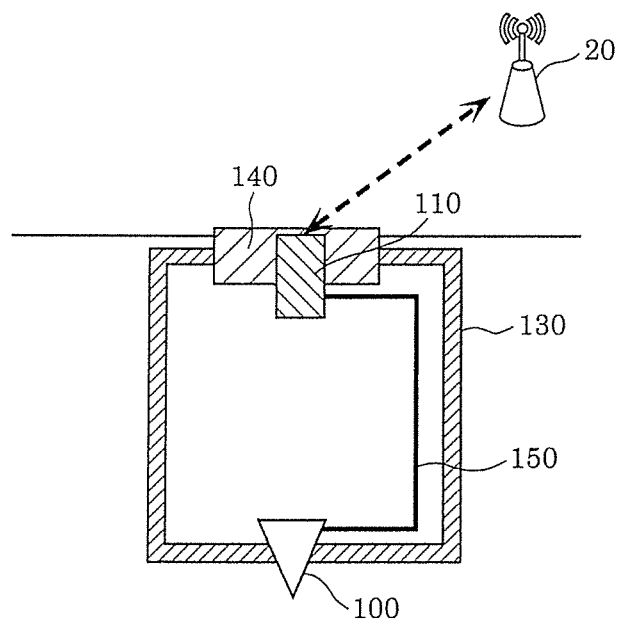
FIG. 7 is a diagram showing a connection between the sensor module and the communication module according to Embodiment 1.

FIG. 7 is a diagram showing a connection between sensor module 100 and communication module 110 according to the present embodiment. As illustrated in FIG. 7, sensor module 100 and communication module 110 are connected by communication wire 150. As stated above, sensor module 100 is disposed in weep hole 131 that is disposed in the base of hand hole 130. Communication module 110 is disposed on lid 140 that faces the base of hand hole 130. As illustrated in FIG. 7, communication wire 150 connects sensor module 100 and communication module 110, and is disposed along a lateral surface of the interior of hand hole 130. Note that communication wire 150 may be imbedded in a wall of hand hole 130.

Sensor module 100 and communication module 110 may each include a wireless communicator and may be wirelessly connected, as will be described later.

3. Operation of Gas Monitoring System

Figure 8:
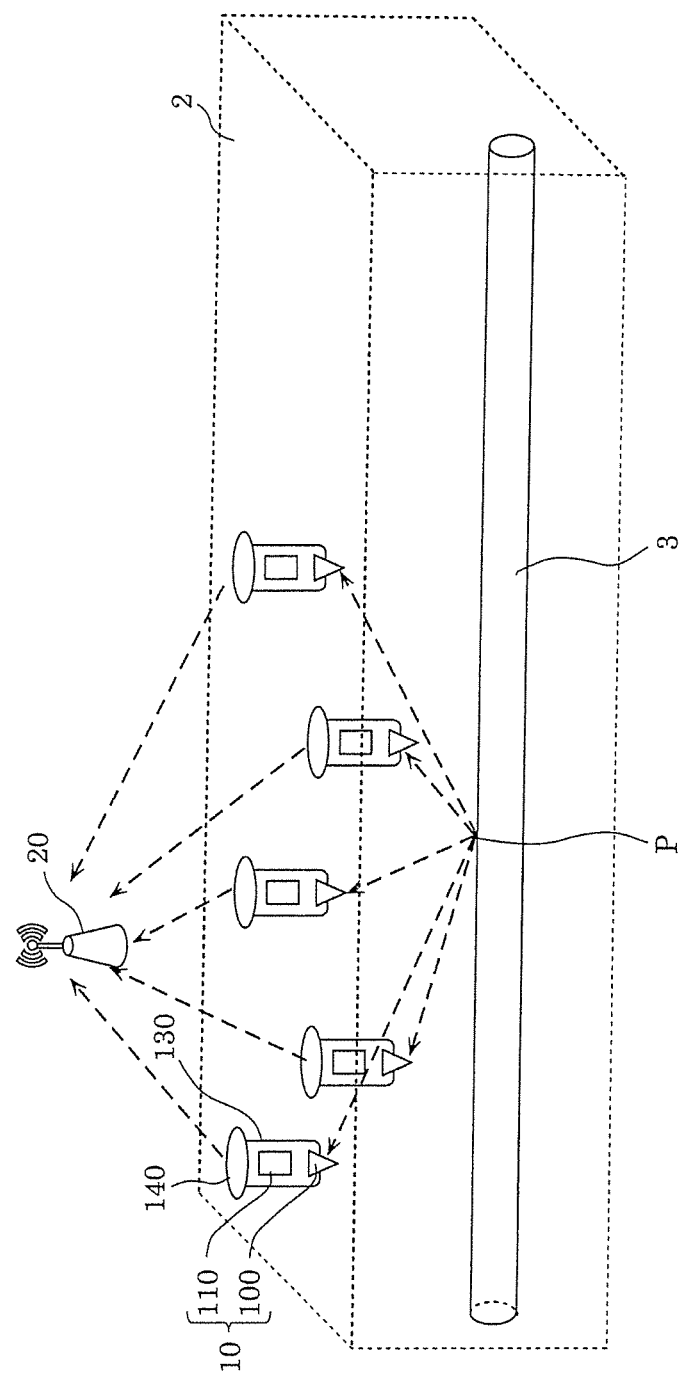
FIG. 8 is a diagram for describing an operation of the gas monitoring system according to Embodiment 1.
Figure 9:
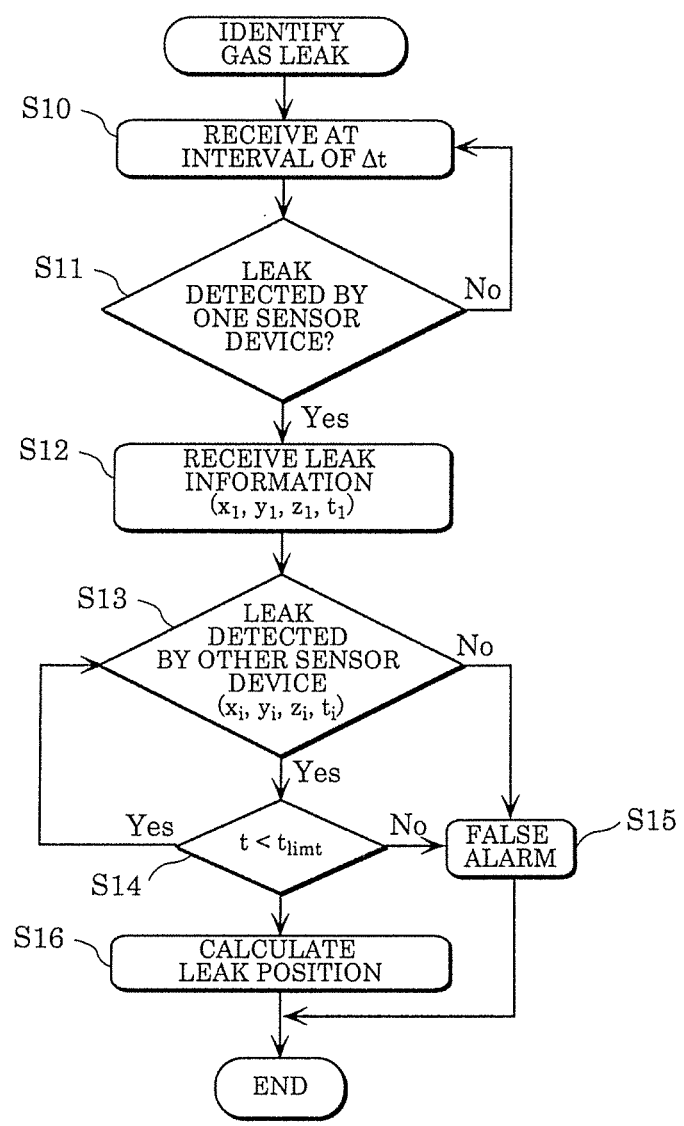
FIG. 9 is a flowchart of a procedure for identifying leaks by the gas monitoring system according to Embodiment 1.

An operation for detecting gas containing hydrogen using gas monitoring system 1 will be described next. FIG. 8 is a diagram for describing the operation of gas monitoring system 1 according to the present embodiment. FIG. 9 is a flowchart of a procedure for identifying leaks by gas monitoring system 1 according to Embodiment 1. In the present embodiment, as illustrated in FIG. 8, a case will be described in which, for example, five sensor devices 10 are associated to one another through one gateway 20.

Note that since multiple sensor devices 10 are disposed, it is possible for another sensor module 100 to detect a position of a gas containing hydrogen leak even when at least one of the multiple sensor modules 100 is malfunctioning.

Note that the multiple sensor devices 10 may be disposed evenly spaced and linearly along and above pipeline 3 disposed in ground 2, and may also be disposed unevenly spaced and non-linearly above pipeline 3, as illustrated in FIG. 1. Hereinafter, an operation of gas monitoring system 1 is described when gas the multiple sensor devices 10 are disposed unevenly spaced and non-linearly. Note that positions of the multiple sensor devices 10 are shown using x-axis, y-axis, and z-axis coordinates, with the x-axis being one horizontal axis, the y-axis being another horizontal axis and perpendicular to the x-axis, and the z-axis being perpendicular to the x-axis and the y-axis. t indicates the time.

Each sensor device 10 communicates with gateway 20 and transmits a gas containing hydrogen detection result to gateway 20. Sensor device 10 and gateway 20 communicate, for example, at intervals of time $\Delta t$. In other words, gateway 20 receives the gas containing hydrogen detection result from sensor device 10 every time $\Delta t$ (step S10). At this point, each sensor device 10 may communicate with sensor device 10 at the same time and may also communicate sequentially.

When a gas containing hydrogen leak is detected by at least one sensor device 10 (Yes in step S11), gateway 20 receives positional information of sensor device 10 along with the gas containing hydrogen leak information as gas containing hydrogen leak information (step S12). The positional information of sensor device 10 is, for example, expressed by the above x-axis, y-axis, and z-axis coordinates. For example, when a gas containing hydrogen leak is detected by sensor device 10 disposed in position $P_1$ shown in FIG. 8, gateway 20 receives the coordinates of position $P_1$ and the time the leak is detected ($x_1$, $y_1$, $z_1$, $t_1$).

Note that sensor device 10 may also transmit ID information instead of the positional information. In this case, gateway 20 may preassociate the ID information and the positional information of each sensor device 10 and store the information in the base station.

When a gas containing hydrogen leak is not detected by the multiple sensor devices 10 (No in step S11), gateway 20 receives the gas containing hydrogen detection result from sensor device 10 once more at the next interval of time $\Delta t$.

When a gas containing hydrogen leak is also detected by another sensor device 10 (Yes in step S13), gateway 20 receives the gas containing hydrogen detection result and the positional information of sensor device 10 as the gas containing hydrogen leak information in the other sensor device 10. For example, when a gas containing hydrogen leak is detected by sensor device 10 disposed in position $P_n$ shown in FIG. 8, gateway 20 receives the coordinates of position $P_n$ and the time the leak is detected ($x_n$, $y_n$, $z_n$, $t_n$). The gas containing hydrogen leak position is then detected using time difference t between (i) time $t_1$ at which the gas containing hydrogen leak is detected by sensor device 10 disposed in position $P_1$ and (ii) time $t_n$ at which the gas containing hydrogen leak is detected by sensor device 10 disposed in position $P_n$.

When time difference t does not exceed preset time $t_{limit}$ (Yes in step S14), gateway 20 calculates the gas containing hydrogen leak position (step S16). At this point, gateway 20 detects the gas containing hydrogen leak position using the GPS module. It is possible to calculate the coordinates of leak P with GPS module using the distance between four satellites and gas containing hydrogen leak P. At this point, the leak position is calculated using an iterative sequential calculation method (Newton's method). Precise description of the calculation method is omitted for being common knowledge.

Gateway 20 determines that gas containing hydrogen is leaking from at a position in pipeline 3 proximate to position $P_1$ using the calculation performed using GPS.

When time difference t does not exceed preset time $t_{limit}$ (No in step S14), gateway 20 determines that there is no gas containing hydrogen leaking at a position in pipeline 3 proximate to position $P_1$, i.e., that there is a false alarm (step S15).

When a gas containing hydrogen leak is also not detected in another sensor device 10 (No in step S13), gateway 20 determines it is a false alarm (step S15).

In this manner, a gas containing hydrogen leak is detected. A gas containing hydrogen leak position is further transmitted from gateway 20 to maintenance service 7 via cloud system 6.

Note that the communication interval between sensor device 10 and gateway 20 may be the same as the gas containing hydrogen detection interval of sensor module 100, and may also be different. When the communication interval between sensor device 10 and gateway 20 is different from the gas containing hydrogen detection interval of sensor module 100, sensor module 100 or communication module 110 in sensor device 10 may temporarily store the gas containing hydrogen detection result in memory 105e or 112c, read the gas containing hydrogen detection result from memory 105e or 112c at the same as time as the communication, and transmit the gas containing hydrogen detection result to gateway 20, as described above.

Sensor device 10 may transmit the gas containing hydrogen detection result to gateway 20 per predetermined period, and may also transmit the detection result to gateway 20 only when gas containing hydrogen is detected.

4. Advantageous Effects, Etc

Gas monitoring system 1 and sensor device 10 according to the present embodiment make it possible to transmit the gas containing hydrogen detection result of sensor module 100 to gateway 20 using communication module 110. The gas containing hydrogen detection result can be reported from gateway 20 to maintenance service 7 via cloud system 6. Since sensor device 10 is disposed in hand hole 130, maintenance service 7 is capable of performing inspection and maintenance of sensor device 10. When sensor device 10 is malfunctioning, maintenance service 7 is capable of replacing sensor device 10. Therefore, gas monitoring system 1 according to the present embodiment enables, maintenance service 7 to monitor for gas leaks at all times.

Embodiment 2

Gas monitoring system 1 according to Embodiment 2 will be described next.

Gas monitoring system 1 according to the present embodiment differs from gas monitoring system 1 described in Embodiment 1 in that sensor module 100a includes communication circuit 109 for wirelessly communicating with communication module 110.

Figure 10:
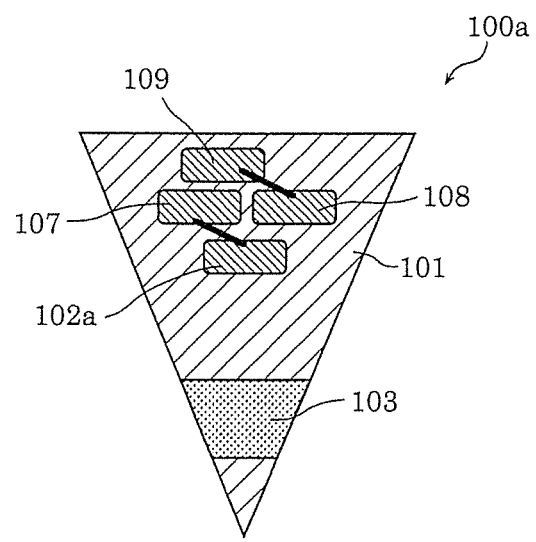
FIG. 10 is a cross-sectional view of a configuration of a sensor module according to Embodiment 2.

FIG. 10 is a cross-sectional view of a configuration of sensor module 100a according to the present embodiment. As illustrated in FIG. 10, sensor module 100a according to the present embodiment includes sensor circuit 102a, power sources 107 and 108, and communication circuit 109.

Sensor circuit 102a has the same configuration as detector 105 of sensor circuit 102 described in Embodiment 1. Sensor circuit 102a does not include power source 106 and operates by being supplied with electric power from power source 107 disposed outside of sensor circuit 102a. In other words, in the present embodiment, power source 107 is the first power source. Sensor circuit 102a is connected to power source 107 by a wire. The configuration of power source 107 is the same as power source 106 described in Embodiment 1, and description thereof is thus omitted.

Sensor module 100a includes communication circuit 109 instead of the communication wire for communicating with communication module 110. Communication circuit 109 allows sensor module 100a to wirelessly communicate with communication module 110. Communication circuit 109 receives the detection result from sensor module 100a with an antenna (not illustrated in the drawings), and further outputs the detection result to communication module 110.

Communication circuit 109 does not include power source 113 unlike communication module 110 described in Embodiment 1, and operates by being supplied with electric power from power source 108 disposed outside of communication circuit 109. In other words, in the present embodiment, power source 108 is the second power source. Communication circuit 109 is connected to power source 108 by a wire. The configuration of power source 108 is the same as the above power source 107, and description thereof is thus omitted.

Figure 11:
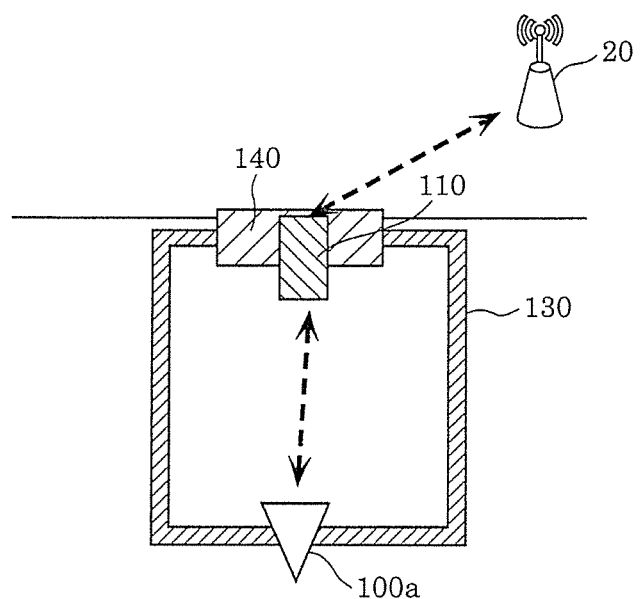
FIG. 11 is a diagram showing a connection between the sensor module and the communication module according to Embodiment 2.

FIG. 11 is a diagram showing a connection between sensor module 100a and communication module 110 according to the present embodiment. As stated above, sensor module 100a is disposed in weep hole 131 that is disposed in the base of hand hole 130. Communication module 110 is disposed on lid 140 that faces the base of hand hole 130. A distance between sensor module 100a and communication module 110 may be any distance as long as sensor module 100a and communication module 110 are capable of wirelessly communicating with each other.

In this manner, the communication between sensor module 100a and communication module 110 may also be performed wirelessly. This makes it possible to increase the freedom of placement between sensor module 100a and communication module 110 since there is no need for a communication wire.

Embodiment 3

Gas monitoring system 1 according to Embodiment 3 will be described next.

Gas monitoring system 1 according to the present embodiment differs from gas monitoring system 1 described in Embodiment 1 in that sensor device 10 is disposed in road rivet 240.

Figure 12:
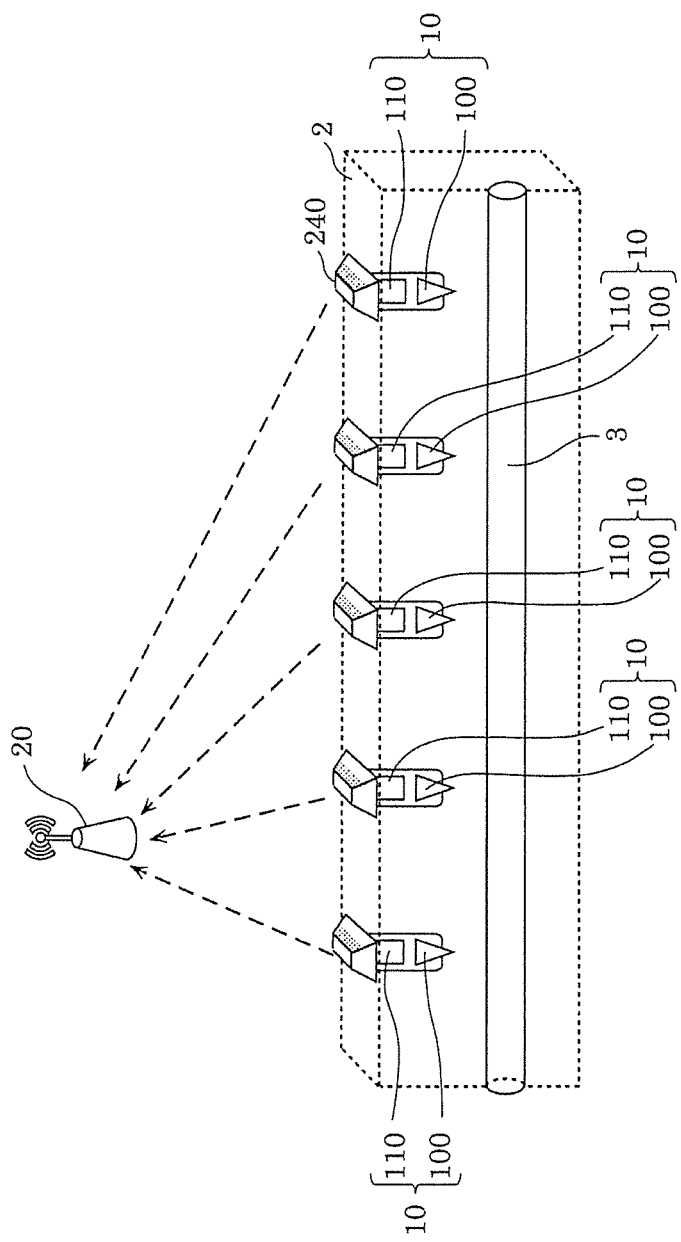
FIG. 12 is an overall diagram of the gas monitoring system according to Embodiment 3.
Figure 13:
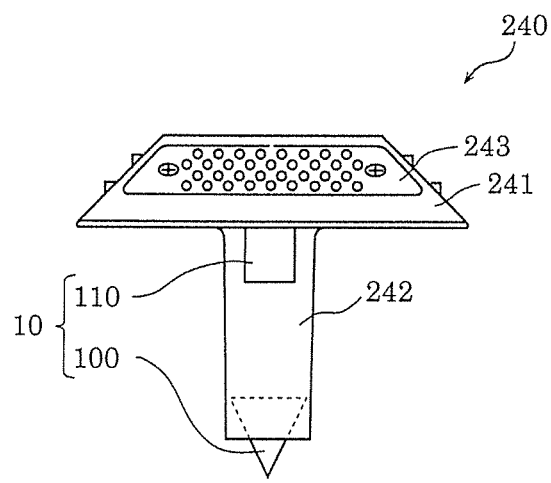
FIG. 13 is a diagram showing an arrangement of the sensor module and the communication module according to Embodiment 3.

FIG. 12 is an overall diagram of gas monitoring system 1 according to the present embodiment. FIG. 13 is a diagram showing an arrangement of sensor module 100 and communication module 110 according to the present embodiment.

In gas monitoring system 1 according to the present embodiment, sensor device 10 is disposed in road rivet 240. Road rivet 240 is a rivet indicating traffic lines, etc., and a portion thereof is buried in ground 2. For example, road rivet 240 is disposed on a centerline of a roadway, a boundary line between a roadway and a service road, etc. at a predetermined interval. Road rivet 240 includes a metal, polycarbonate resin, etc., and, as illustrated in FIG. 12, sensor module 100 and communication module 110 included in sensor device 10 are disposed in the portion of road rivet 240 that is buried in ground 2.

As illustrated in FIG. 13, road rivet 240 includes body 241, leg 242, and reflection plate 243. Leg 242 is disposed below body 241 and is buried in ground 2. Body 241 is disposed on the surface of ground 2. Reflection plate 243 is disposed on body 241 in a position where reflection plate 243 can be easily seen by pedestrians walking and drivers driving on a roadway and service road.

Sensor module 100 is disposed at a distal end of leg 242 of road rivet 240, and a subulate end portion thereof protrudes from leg 242. With this, the distal end of sensor module 100 contacts ground 2 when buried in ground 2. Communication module 110 of sensor device 10 is disposed in leg 242 more proximate to the surface than sensor module 100. Note that communication module 110 may also be disposed on body 241.

With this, sensor module 100 is disposed more proximate to pipeline 3, which transports gas containing hydrogen, than communication module 110. Since communication module 110 is disposed more proximate to the surface than sensor module 100, communication module 110 can easily communicate with gateway 20. Sensor module 100 and communication module 110 may be connected by a communication wire and communicate through communication wire similar to sensor device 10 described in Embodiment 1, and may also communicate wirelessly.

Note that sensor module 100 and communication module 110 may both be disposed in road rivet 240, and also only the sensor module may be disposed in road rivet 240. Sensor module 100 and communication module 110 may be integrally disposed in road rivet 240, and as illustrated in FIG.

13, may be disposed separately in leg 242 of road rivet 240 proximate to the distal end thereof and leg 242 proximate to the surface or body 241. Road rivet 240 is not limited to the shape shown in FIG. 13, and may be any other shape.

Embodiment 4

Gas monitoring system 1 according to Embodiment 4 will be described next.

Gas monitoring system 1 according to the present embodiment differs from gas monitoring system 1 described in Embodiment 1 in that at least one of sensor module 100 and communication module 110 detect malfunctions.

Sensor module 100 and communication module 110 communicate with each other at a predetermined time interval, and a detection result by sensor module 100 about whether or not gas containing hydrogen is detected is transmitted from sensor module 100 to communication module 110.

When sensor module 100 cannot communicate with communication module 110 for a certain length of time, it is determined that communication module 110 is malfunctioning. When it is determined that communication module 110 is malfunctioning, sensor module 100 accumulates the gas containing hydrogen detection result in memory 105e. When communication module 110 is no long malfunctioning and communication between sensor module 100 and communication module 110 is restored, sensor module 100 then transmits the gas containing hydrogen detection results stored in memory 105e to communication module 110. At this point, sensor module 100 may transmit only detection result information about when gas containing hydrogen is detected to communication module 110, and may also transmit all detection results to communication module 110.

When communication module 110 cannot communicate with sensor module 100 for a certain length of time, it is determined that sensor module 100 is malfunctioning. Communication module 110 then transmits a determination result to gateway 20. The determination result is further transmitted from gateway 20 to maintenance service 7 via cloud system 6. This enables maintenance service 7 to detect an anomaly in sensor module 100.

Embodiment 5

Gas monitoring system 1 according to Embodiment 5 will be described next.

Gas monitoring system 1 according to the present embodiment differs from gas monitoring system 1 described in Embodiment 1 in that sensor module 100 includes a humidity sensor as the second sensor.

Illustration of the humidity sensor is omitted, but is disposed proximate to the top of the conical casing 101 of sensor module 100. It is possible to detect the humidity of ground 2 since the top of casing 101 of sensor module 100 contacts ground 2.

Sensor module 100 determines sensor module 100 to be immersed in water when a humidity detected by the humidity sensor is at least 90%. This enables sensor module 100 to detect an anomaly in sensor module 100 before sensor module 100 is fully immersed in water (humidity 100%). Therefore, it is possible to prevent sensor module 100 from malfunctioning beforehand since maintenance service 7 is capable of detecting that sensor module 100 is immersed in water beforehand.

Note that in the present embodiment, a humidity detected by the humidity sensor of at least 90% means being immersed in water, but is not limited thereto, and may be suitably changed in accordance with the environment in which sensor module 100 is disposed.

Embodiment 6

Gas monitoring system 1 according to Embodiment 6 will be described next.

Gas monitoring system 1 according to the present embodiment differs from gas monitoring system 1 described in Embodiment 1 in that sensor module 100 and communication module 110 include a power-generating device as electric power source. The power-generating device is, for example, a power-generating panel that generates solar power.

Figure 14:
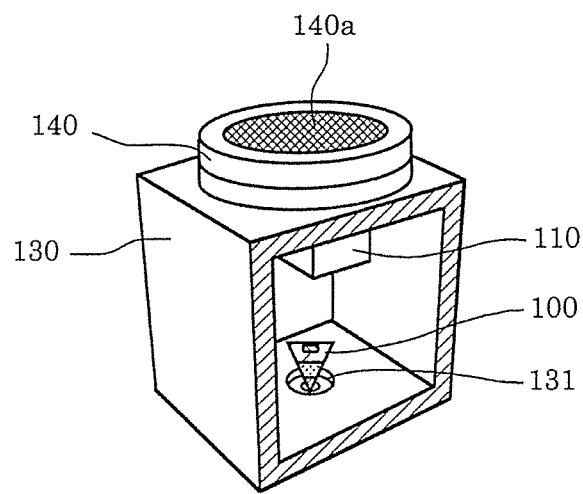
FIG. 14 is a diagram showing another example of the sensor device according to Embodiment 6.

FIG. 14 is a diagram showing another example of sensor device 10 according to the present embodiment. As illustrated in FIG. 14, sensor device 10 according to the present embodiment includes panels 140a on an upper surface of lid 140 for generating solar power. Panels 140a charge battery 113a of communication module 110 disposed on a bottom surface of lid 140, i.e., inside hand hole 130. This enables communication module 110 to communicate with gateway 20 using the electric power generated through the solar power generation. Note that communication module 110 may use the electric power generated through the solar power generation to communicate with sensor module 100.

Note that the electric power generation through the solar power generation is not limited to charging battery 113a of communication module 110, and may also charge battery 106a of sensor module 100. Another electric storage device for storing the electric power generated through the solar power generation may be disposed instead of battery 106a and battery 113a.

Note that the electric power source of the sensor module and the communication module is not limited to being a solar power-generating device, and may also be, for example, another power-generating device, e.g. a power-generating device that uses vibration.

The electric power source of sensor module 100 and communication module 110 may include a power-generating device, and either sensor module 100 or communication module 110 may also include a power-generating device. Sensor module 100 and communication module 110 may both use the same power-generating device, and may also include different power-generating devices.

Other Embodiments

A gas sensor and gas detection system according to several aspects of the present disclosure has been described above based on the embodiments, but the present disclosure is not limited to these embodiments. Forms obtained by various combinations of the components in the different embodiments that can be conceived by a person skilled in the art which are within the scope of the essence of the present disclosure may also be included in the scope of the several aspects of the present disclosure.

For example, the above gas sensor is described as a hydrogen sensor that detects gas containing hydrogen, but may be a gas sensor that detects any gas other than gas containing hydrogen.

The above sensor device is not limited to being disposed in the hand hole, and may also be disposed, for example, in a manhole in which a person can enter.

A second sensor device is not limited to being a temperature sensor, humidity sensor, pressure sensor, and water immersion sensor, and may be a sensor that detects other useful parameters for preventing damage to the sensor device.

Since the gateway includes the GPS module, the gas monitoring system may identify, using GPS, a sensor module that detects parameters with the second sensor.

The sensor device is not limited to being conical or pyramidal, and may be any other shape.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

A gas sensor according to the present disclosure is useful for a hydrogen transportation route that requires monitoring for gas leaks at all times, and, for example, a hydrogen sensor that detects hydrogen leaks from a pipeline that supplies hydrogen gas, and the like.

What is claimed is:

1. A sensor device that detects a gas leak underground, the sensor device comprising:
    a sensor module including a first sensor that detects gas;
    a processing circuit that processes a detection result outputted from the first sensor;
    a communication module that communicates with the sensor module and transmits information processed by the processing circuit exteriorly of the sensor device;
    a first power source that is an electric power source of the sensor module; and
    a second power source that is an electric power source of the communication module,
    wherein the sensor module further includes a casing at least part of which is buried underground and that includes a tip portion in a downward conical shape, and a waterproof filter or a dustproof filter,
    the first sensor is disposed in the casing, and
    the waterproof filter or the dustproof filter is disposed in a position that is below the first sensor in the tip portion of the casing and at which an inner space of the tip portion is filled with the waterproof filter or the dustproof filter when the tip portion is viewed from a vertical direction.

2. The sensor device according to claim 1, wherein the sensor module includes:
    the processing circuit; and
    the first power source that supplies electric power to the first sensor and the processing circuit.

3. The sensor device according to claim 1, wherein the first sensor is a hydrogen sensor that detects hydrogen molecules.

4. The sensor device according to claim 1, further comprising:
    a second sensor that detects at least one parameter relating to a surrounding environment of the sensor device.

5. The sensor device according to claim 4, wherein the second sensor is disposed below the first sensor.

6. The sensor device according to claim 4, wherein the second sensor is at least any of a temperature sensor, a humidity sensor, and a pressure sensor.

7. The sensor device according to claim 4, wherein the second sensor is a water immersion sensor that detects that the sensor module is immersed in water.

8. The sensor device according to claim 4, wherein
    the second sensor is a humidity sensor, and
    the sensor modules determines the sensor module to be immersed in water when a humidity detected by the humidity sensor is at least 90%.

9. The sensor device according to claim 2, wherein at least a portion of the casing is conical or pyramidal.

10. The sensor device according to claim 1, wherein the communication module is disposed above the sensor module.

11. The sensor device according to claim 1, wherein the sensor module corresponds to the communication module.

12. The sensor device according to claim 1, wherein
    the sensor module comprises a plurality of sensor modules, and
    the communication module corresponds to the plurality of sensor modules.

13. The sensor device according to claim 1, wherein the sensor module and the communication module are integrally disposed.

14. The sensor device according to claim 1, wherein the sensor module and the communication module are separately disposed.

15. The sensor device according to claim 14, wherein the sensor module and the communication module are connected by a communication wire.

16. The sensor device according to claim 14, wherein the sensor module and the communication module are wirelessly connected.

17. The sensor device according to claim 1, wherein the sensor module transmits the detection result to the communication module a plurality of times.

18. The sensor device according to claim 1, wherein the sensor module outputs each instance of the detection result to the communication module.

19. The sensor device according to claim 1, wherein the sensor module outputs the detection result of the communication module only when gas is detected.

20. The sensor device according to claim 1, wherein the sensor module encrypts the detection result and outputs the detection result encrypted to the communication module.

21. The sensor device according to claim 1, wherein a detection interval of the gas by the sensor module and a transmission interval of the detection result from the sensor module to the communication module differ.

22. The sensor device according to claim 1, wherein the sensor module includes a first memory that stores the detection result, and encrypts and stores the detection result in the first memory.

23. The sensor device according to claim 1, wherein the communication module includes a second memory that stores the detection result, and stores the detection result received from the sensor module in the second memory.

24. The sensor device according to claim 1, wherein at least one of the first power source and the second power source includes a power-generating device.

25. A gas monitoring system that detects a gas leak underground, the gas monitoring system comprising:
    at least one sensor device that detects gas and outputs a detection result; and a gateway that receives the detection result, wherein
the at least one sensor device includes:
 a sensor module having a first sensor that detects gas;
 a processing circuit that processes the detection result outputted from the first sensor;
 a communication module that communicates with the sensor module and transmits information processed by the processing circuit exteriorly of the at least one sensor device;
 a first power source that is an electric power source of the sensor module; and
 a second power source that is an electric power source of the communication module,
wherein the sensor module further includes a casing at least part of which is buried underground and that includes a tip portion in a downward conical shape, and a waterproof filter or a dustproof filter,
the first sensor is disposed in the casing, and
the waterproof filter or the dustproof filter is disposed in a position that is below the first sensor in the tip portion of the casing and at which an inner space of the tip portion is filled with the waterproof filter or the dustproof filter when the tip portion is viewed from a vertical direction.

26. The gas monitoring system according to claim 25, wherein the first sensor is a hydrogen sensor that detects hydrogen molecules.

27. The gas monitoring system according to claim 25, wherein a portion of the sensor module is disposed inside a hand hole of which at least a portion is buried underground.

28. The gas monitoring system according to claim 27, wherein the sensor module is disposed in a weep hole in the hand hole.

29. The gas monitoring system according to claim 25, wherein the sensor module is disposed in a rivet of which at least a portion is buried underground.

30. The gas monitoring system according to claim 25, wherein the sensor module is disposed above a transportation route of the gas underground.

31. The gas monitoring system according to claim 25, wherein
 the sensor module comprises a plurality of sensor modules, and
 the plurality of sensor modules are disposed unevenly spaced or non-linearly.

32. The gas monitoring system according to claim 25, wherein
 the sensor module comprises a plurality of sensor modules, and
 a position of the gas leak is calculated using a difference in detection time of the gas by the plurality of sensor modules.

33. The gas monitoring system according to claim 25, further comprising:
 a Global Positioning System (GPS) module, wherein a position of the gas leak is calculated using the GPS module.

34. The gas monitoring system according to claim 33, wherein the GPS module is disposed in the gateway.

35. The gas monitoring system according to claim 33, wherein
 the sensor module further includes a second sensor that detects at least one parameter relating to a surrounding environment of the at least one sensor device, and
 the sensor module that detects the at least one parameter using the second sensor is identified using the GPS module.

36. The gas monitoring system according to claim 25, wherein the communication module determines the sensor module to be malfunctioning when the sensor module and the communication module are not capable of communicating for a certain length of time.

37. The gas monitoring system according to claim 36, wherein the communication module transmits a determination result to the gateway when the communication module determines that the sensor module is malfunctioning.

38. The gas monitoring system according to claim 25, wherein the sensor module determines the communication module to be malfunctioning when the sensor module and the communication module are not capable of communicating for a certain length of time.

39. The gas monitoring system according to claim 25, wherein
 the sensor module comprises a plurality of sensor modules, and
 a position of the gas leak is calculated even when at least one of the plurality of sensor modules is malfunctioning.

40. The sensor device according to claim 1, wherein the waterproof filter or the dustproof filter is completely below the first sensor when viewed from the vertical direction.

41. The gas monitoring system according to claim 25, wherein the waterproof filter or the dustproof filter is completely below the first sensor when viewed from the vertical direction.

* * * * *